US00PP25564P3

(12) United States Plant Patent

Maillard et al.

(10) Patent No.: US PP25,564 P3

(45) Date of Patent: May 19, 2015

(54) CHERRY TREE NAMED 'FIRELAM'

(50) Latin Name: ***Prunus avium* (L.) L.**
Varietal Denomination: FIRELAM

(71) Applicant: Agro Selections Fruits, Elne (FR)

(72) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 145 days.

(21) Appl. No.: 13/815,925

(22) Filed: Mar. 18, 2013

(65) Prior Publication Data

US 2013/0263335 P1 Oct. 3, 2013

(30) Foreign Application Priority Data

Apr. 2, 2012 (QZ) ..... PBR 20120750

(51) Int. Cl.
*A01H 5/00* (2006.01)

(52) U.S. Cl.
USPC ..... Plt./181

(58) Field of Classification Search
USPC ..... Plt./181
See application file for complete search history.

*Primary Examiner* — Susan McCormick Ewoldt
(74) *Attorney, Agent, or Firm* — Westerman, Hattori, Daniels & Adrian, LLP

(57) ABSTRACT

A new and distinct variety of cherry tree denominated 'FIRELAM' has fruits with large size and dark red skin color, very firm, and with a good flavor and eating quality; the fruit is further characterized by its good handling and storage qualities.

4 Drawing Sheets

Latin name of the genus and species of the plant claimed: *Prunus avium* (L.) L.

Variety denomination: 'FIRELAM'.

This application claims priority of Community plant variety right No. 2012/0750 filed on Apr. 2, 2012 (Apr. 2, 2012) which is hereby incorporated by reference in its entirety.

BACKGROUND OF THE NEW VARIETY

1. Field of the Invention

In the field of plant genetics, we conduct an extensive and continuing plant-breeding program including the organization and reproduction of orchard trees, among which peaches, nectarines, apricots, apples, and cherries are exemplary. It was against this background of our activities that the present variety of cherry tree was originated and reproduced by us in our experimental orchard located near Elne, Pyrénées Orientales department (an administrative district), France.

2. Origin of the Variety

The present invention relates to a new a distinct variety of cherry tree *Prunus avium* L. which has been given the variety denomination 'FIRELAM'. This tree produces fruits with a long shelf life without alteration both on the trees after growth completion and after harvesting, very good eating quality with a red flesh for fresh market in June in the Pyrénées Orientales department, France. Contrast is made to 'FOLFER' cherry tree (non patented) and to 'RUBILAM' cherry tree (U.S. Plant Pat. No. 23,798) for reliable description. 'FIRELAM' is a promising candidate for commercial success in that it produces very attractive fruits having a long shelf life.

The present new variety of cherry tree (*Prunus avium* L.) was developed by us in our experimental orchard located in France. 'FIRELAM' cherry tree originated in a cultivated area of the South of France, in the Pyrénées-Orientales department where it was also tested. This zone also called Roussillon is subject to a Mediterranean climate. The winter is generally mild, that is to say the total amount of cold hours lower than 7° C. (Celsius) varies from 600 hours to 1200 hours. The summer is hot and dry, that is to say the total amount of sunshine hours is an average of 2400 hours to 2800 hours per year. The prevailing wind is called "Tramontane": it dries the air and clear the sky from cloud but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen and the summer is dry with a few thunderstorms.

The 'FIRELAM' variety resulted from an open pollination of the cherry tree variety named 'INRA 3364' (non patented) which was used as the seed parent. Thus, the pollen parent is unknown.

'FIRELAM' variety was provisionally designated, tested and genetically identified by a genetic profile under number 02.14.52CE-ASF0607 and was registered at the Official Catalogue of the Agricultural Ministry of the French Republic on Nov. 27, 2011, under the number 4049394. The 'FIRELAM' variety was obtained by hybridizing and propagated by grafting on a 'Maxma 14' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

SUMMARY OF THE NEW VARIETY

The new variety 'FIRELAM' produces fruits of large size, very firm, with a semi-sweet flavor, low acidity, and a dark red color. The blooming period is semi-early for the variety, namely at the end of March. The maturity period is late, generally from end of May to beginning of June in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
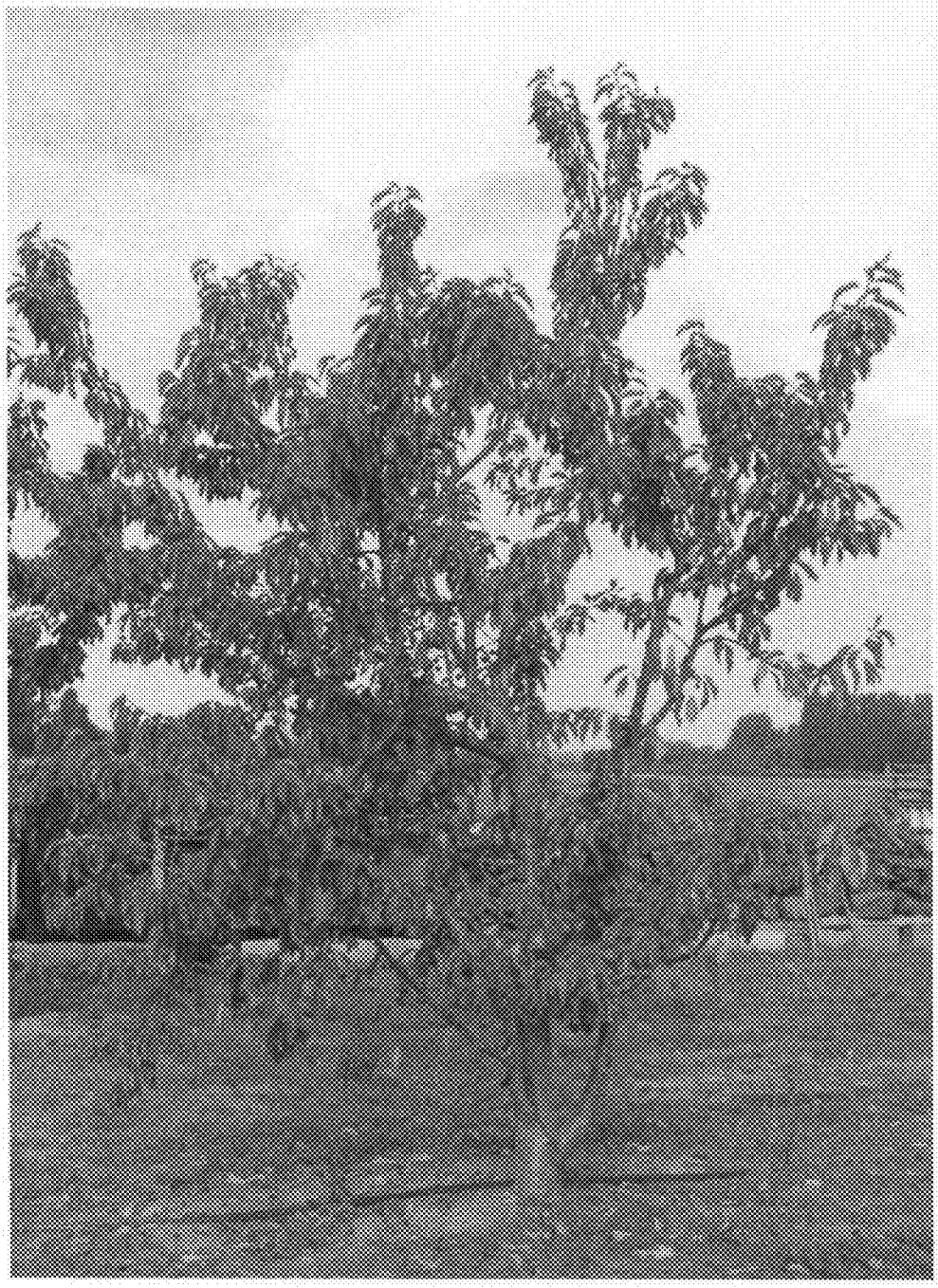
FIG. 1 is a color photograph which shows a view of a tree of the new variety in orchard, bearing fruits.
Figure 2:
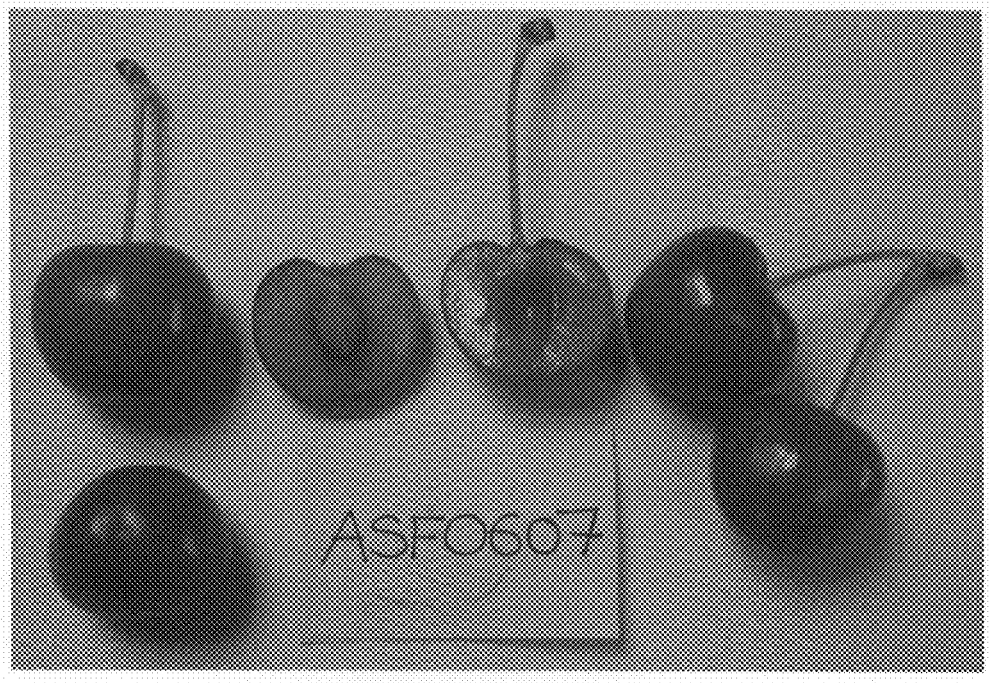
FIG. 2 is a color photograph which shows four whole fruits of the new variety, and a fifth fruit, cut in a half, with the stone being left in one of the halves, for depicting the fruit flesh, the pit, and the pit cavity of the new variety.
Figure 3:
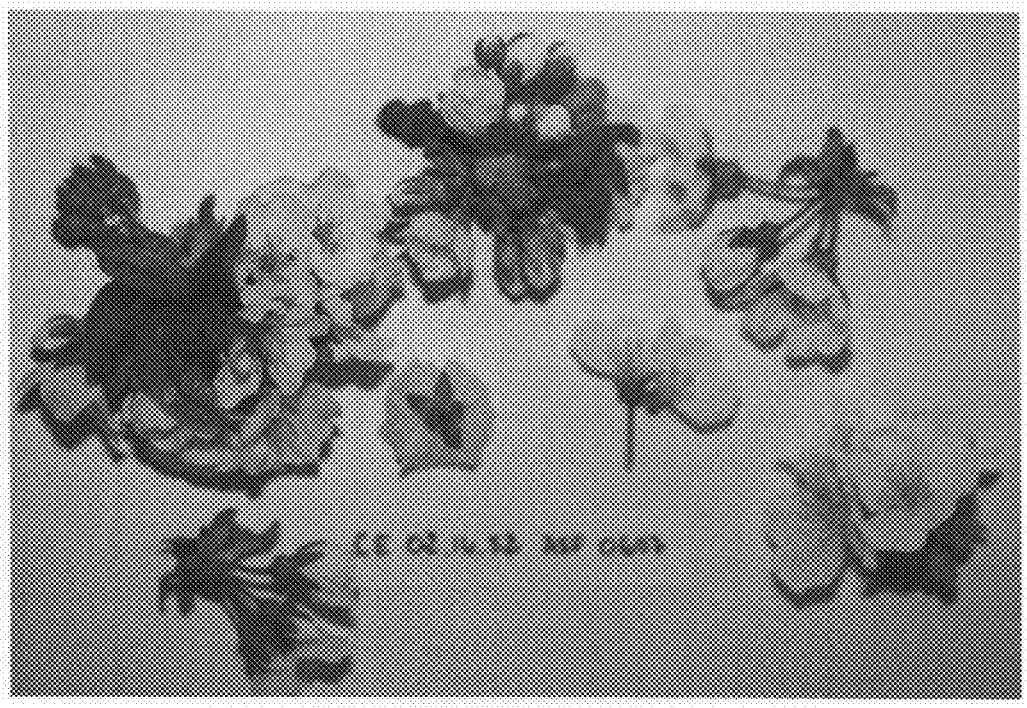
FIG. 3 shows typical white flowers of 'FIRELAM' variety at blooming with some leaves for depicting the flower buds at different stages of development; and the reverse and side view of the flowers and the reproductive organs with petals removed, of the new variety.
Figure 4:
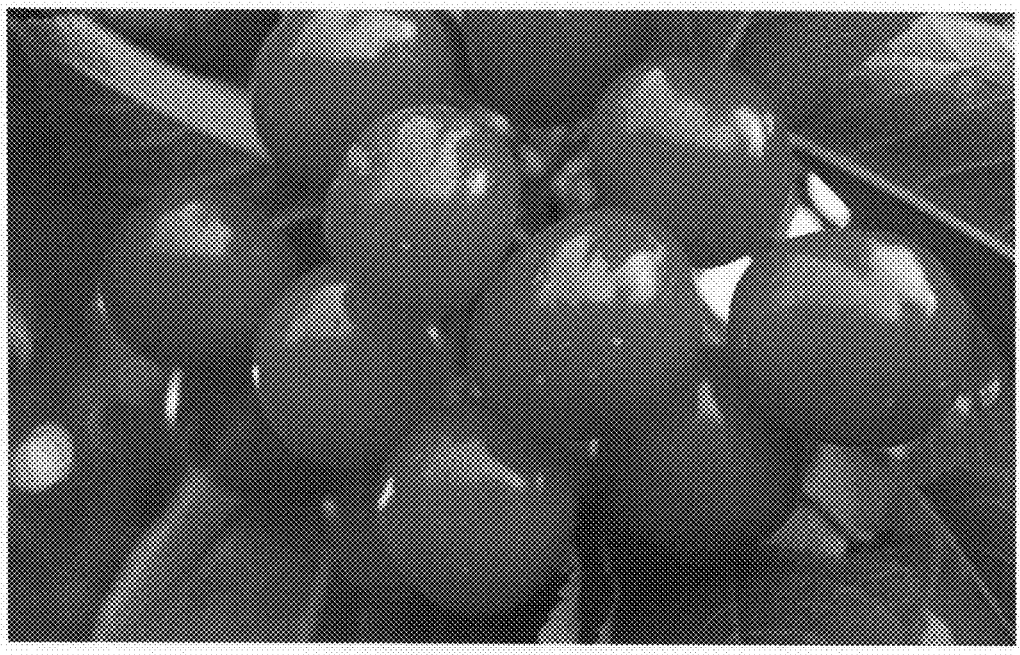
FIG. 4 is a color photograph that shows a close view of typical fruits of the new variety 'FIRELAM' at ripening time.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of cherry tree, its flowers, foliage and fruit, as based on observations of specimens grown near Elne, South of France, with color in accordance with The R.H.S. Colour Chart (Fourth Edition) provided by The Royal Horticultural Society of Great Britain.

The trees, flowers and fruits may vary in slight detail due to variations in soil type, cultural practices and climatic conditions.

The main characteristics of this new variety of sweet cherry are a large or very large fruit size with a color of skin considered dark red. The fruit flesh is medium red on cream. The fruit is very firm.

The time of beginning of flowering is semi-early whereas the time of beginning of fruit ripening is considered late.

In comparison with the cherry tree 'FOLFER' (non-patented), the present variety 'FIRELAM' ripens generally 14 days later and blooms approximately at the same time with a more staggered blooming period.

Compared to 'RUBILAM' (U.S. Plant Pat. No. 23,798) cherry tree, 'FIRELAM' blooms approximately 5 days earlier and ripens 9 days later than 'RUBILAM'.

Concerning the resistance to pests and diseases 'FIRELAM' is low sensitive to *Monilia*.

DETAILED DESCRIPTION

Referring more specifically to the pomological details of this new and distinct variety of cherry tree, the following has been observed on trees on their fifth growing season (fourth year of production) under the ecological conditions prevailing at the orchards located near the town of Elne, Pyrénées-Orientales department, France.

All observations have been done on rootstock cultivar. The rootstock was a "MAXMA 14" tree. All major color code designations are by reference to The R.H.S. Colour Chart 2001 (Fourth Edition) provided by The Royal Horticultural Society of Great Britain.

Tree:

*Generally*.—The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical and the diameter is limited to 2 meters. Size. Medium to high as compared to other commercial sweet cherry cultivars. The tree size the first year was approximately 2.50 meters. The tree was pruned during each following dormant season to a height of approximately 2.50 meters. Current seasons shoots growth could reach 0.80 meters. So the tree size from the second year (second and next years) reached a final height of 3.10 to 3.30 meters with current seasons shoots length comprised. Spread. Approximately 2.0 meters with a cylindrical shape. The whole orchard was oriented to a central leader organization, with tree lines spaced of 4.0 meters and trees spaced of 1 meter in a same tree line. Vigor. Medium, tree growth reaching 0.60 to 0.80 meters the first growing season. Productivity. Good to very good productivity, every year. The new variety produces adequate fruit set annually on a regular basis. The number of the fruit set varies with the prevailing climatic conditions and cultivar practices employed during the bloom period, and is therefore not distinctive of the present variety. Bearer. Very regular and quantitative. The extinction of the clusters of May improves the calibre and firmness of the fruit. Form. Naturally spreading to semi-upright. Hardiness. Hardy in all stone fruit growing areas of France and especially where the chilling requirement is between 350 and 1200 hours. No injury with a temperatures as low as −12° C. in winter. Good resistance to late frosts.

*Trunk*.—Size. Medium. Measured between 100 and 115 millimeters above 20.0 centimeters from ground, on $5^{th}$ growing season. Bark texture. Smooth to rough, due to the lenticels. Lenticels. High number of lenticels. The number of lenticels reaches 3 to 4 lenticels per $cm^2$. At the $5^{th}$ growing season, lenticels are 2.5 to 4.0 millimeters in height and 6.0 to 12.0 millimeters in width. Lenticels color. Color of lenticels is RHS Greyed Orange N167 B or RHS Greyed Orange N170 A. Bark color. Grey silver brown (RHS Greyed Orange 166 A or RHS Greyed Orange 177 A).

*Branches*.—Size. Medium to large for the new growth. Medium to large for the branches at the $5^{th}$ growing season. Diameter. Average diameter of 35.0 to 50.0 millimeters. Surface texture. Smooth. Wood that is several years old has no furrowed appearance. Color. Old growth is brown (RHS Brown 200 B). Current season shoots: Diameter. Average diameter from 5.0 to 9.0 millimeters. Surface texture. Smooth. Wood that is several years old has no furrowed appearance. Crotch angles. Primary branches are considered variable, but the crotch angles are generally between 75 degrees and 85 degrees from the horizontal axis. This particular characteristic is not considered distinctive of the variety, however. Internode. Generally from 52.0 millimeters to 70.0 millimeters length. Color. New growth is orange brown more or less dark (RHS Greyed Orange 165 A or RHS Greyed Orange 166 A).

Leaves:

*Size.*—Medium for the species. Leaf measurements have been taken from vigorous, upright, current-season growth at approximately mid-shoot. The ratio leaf length/leaf width is 2.05.

*Length.*—From 123.0 to 144.0 millimeters with leaf petiole. Average length with petiole 135.0 millimeters.

*Width.*—From 58.0 to 74.0 millimeters. Average width 66.0 millimeters.

*Leaf form in cross view.*—Concave.

*Leaf form.*—Lanceolate to spatulate (spoon-shaped) with an elliptic shape.

*Apex.*—Acuminate.

*Leaf color.*—Upper leaf surface. Dark green (RHS GREEN 137 A). Lower surface. A lighter green than the upper leaf surface (RHS YELLOW GREEN 147 B). Leaf texture. Smooth and glabrous. The lower surface is also smooth. Leaf venation. Pinnately veined.

*Mid-vein.*—Color. Light green with a yellow touch (RHS YELLOW GREEN 144 D or RHS YELLOW GREEN 145 B to C) and evolves with maturity. Leaf margins. Slightly undulating. Form. Considered slightly dentate. Uniformity. Leaves are isolated.

*Leaf petioles.*—Size. Considered medium to long. Length. About 40.0 to 52.0 millimeters. Diameter. About 2.0 millimeters. Color. Upper surface pale red (RHS GREYED PURPLE N186 C or RHS GREYED BROWN N199 B). Lower surface light green (RHS YELLOW GREEN 145 A). Ratio blade length/petiole length. More or less 2.93.

*Leaf glands.*—Size. Considered medium. Their length is about 2.0 millimeters. Number. Generally 2. Type. Reniform. Color. Orange brown (RHS GREYED ORANGE 165 B or 166 B).

*Leaf stipules.*—Generally. No leaf stipules were observed.

Flowers:

*Flower buds.*—Generally. At pre-floral stage of development, the floral bunches are make up with 4 to 8 floral buds having a conic shape with a round tip. Their form is evolving until blooming, with variables dimensions. Just before blooming, floral buds are approximately 7.0 millimeters wide and approximately 16.0 millimeters long. Color. This characteristic is dependent upon the proximity to bloom. At pre-floral stage of development, the bottom of the flowers buds, or calyx formed by sepals, is of green color (RHS GREEN 138 A to C or RHS YELLOW GREEN 145 A to B) with brown areas (RHS GREYED RED GROUP 179 B to C); the corolla formed by petals, is generally pure white (RHS WHITE 155 D). Hardiness. The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer. Date of bloom. Generally late March. The first bloom was observed on Mar. 31 until Apr. 9, 2007. Last fourth blooms took place respectively from Mar. 23 until Apr. 4, 2009, then from Apr. 4 to Apr. 14, 2010 (exceptionally late due to winter climatic conditions in March 2010), from Mar. 21 to Apr. 1, 2011 and from Mar. 31 to Apr. 8, 2012. Blooming time. Considered semi-early in relative comparison to other commercial cherry cultivars grown in the Pyrénées-Orientales department, France. The date of full bloom is observed at the middle of the blooming period. The date of bloom varies slightly with climatic conditions and cultural practices. Blooming period. Average 10 days. This characteristic varies slightly with the prevailing climatic conditions. Flower type. The variety is considered to have a showy type flower. Flower size. Considered large. Average diameter between 30.0 and 38.0 millimeters when totally opened. Bloom quantity. Considered abundant, approximately 60 flowers per meter. Flower bud frequency. Generally 3 to 5 flower buds appear per node.

*Petal.*—Size. Considered medium for the species. Length. Generally about 16.2 millimeters. Width. Generally about 14.2 millimeters. Petal form. Large form, elliptic, usually slightly overlapping. Petal count. Nearly always 5. Petal texture. Smooth and soft. Petal color. Pure white color (RHS WHITE 155 D) on both surfaces. Fragrance. Very soft.

*Petal claw.*—Form. The claw is considered to have a conic form with a slightly rounded tip. Length. Approximately 7.0 millimeters. Width. Approximately 4.0 millimeters. Petal margins. Smooth with a very slightly undulating.

*Petal apex.*—Generally. The petal apices are generally wide dome shaped.

*Flower pedicel.*—Length. Considered medium to long and having an average length of approximately 16.0 to 25.0 millimeters. Diameter. Average 1.0 millimeter. Color. Green (RHS YELLOW GREEN 144 A to B).

*Calyx.*—Internal surface texture. Smooth and glabrous. Color. The inner surface is yellow green (RHS YELLOW GREEN 151 A to B). The outer surface of the calyx is green (RHS YELLOW GREEN 144 A to B) with pink purple zones (RHS GREYED RED 179 B to C).

*Sepals.*—Surface texture. The outer surface has a thin texture. Size. Usually considered medium. Elliptic shape. Color. The upper surface is green (RHS YELLOW GREEN 144 A to B) with pink purple zones (RHS GREYED RED 179 B to C). Average number of stamens per flower. Between 35 and 39 stamens per flower.

*Anthers.*—Length. Medium. Form. Cardioid. Position of stamens relative to petals. Below. Color. Yellow orange red color (RHS GREYED ORANGE 163 B to C). The color evolves with flowering. Pollen production. Pollen is abundant, and has a yellow color (RHS YELLOW ORANGE 17 B to C) that varies with maturity. The fertility has not been check yet. However, because of the considerable amount of pollen that is product, the pollination is performed as expected.

*Filaments*.—Size. Variable in length, approximately between 8.0 and 12.0 millimeters in length. Color. Considered as white (RHS WHITE 155 D).

*Pistil*.—Number. Usually 1. Length. Approximately from 15.0 to 16.0 millimeters including the ovary, that is slightly longer than stamens length. Color. Considered very pale green (RHS YELLOW GREEN 149 B to C). The color is evolving with flowering. Surface texture. Glabrous. Pubescence. Absent.

*Type of reproduction*.—Pollination.

Fruits:

*Maturity when described*.—Very firm at maturity.

*Date of first picking*.—Jun. 2, 2007 varies slightly with climatic conditions. Particularly late in 2010 because March 2010 was very cold.

*Date of last picking*.—Jun. 8, 2007 varies slightly with climatic conditions. Particularly late in 2010 because March 2010 was very cold. Last known picking times carry on from Jun. 1 to Jun. 5, 2008, then from May 28 to Jun. 5, 2009, then from Jun. 11 to Jun. 14, 2010, then from May 23 to May 27, 2011 and from Jun. 7 to Jun. 14, 2012.

*Ripening period*.—Approximately 4 to 6 days.

*Size*.—Generally. Considered large, with a homogeneous size between them. Clusters of 1 to 3 fruits. Average cheek diameter. About 26.0 to 29.0 millimeters. Average axial diameter. About 23.0 to 25.0 millimeters. Typical weight. Generally about 11.5 to 12.0 grams. This characteristic is highly dependent upon the prevailing cultural practices, and therefore is not particularly distinctive of the variety.

*Fruit form*.—Generally. Reniform to slightly cardioid. Fruit suture. Wide mouthed, extending from the base to the apex. No apparent callousing or stitching exists along the suture line. Without mucrons that is to say the fruit is not mucronate and does not have a proeminence like a tip.

*Suture*.—Color. This has generally a color similar to the blush fruit color, a homogenous red (RHS RED 53 A or RHS RED 46 A).

*Ventral surface*.—Form. Smooth. Apex. In slight depression, very small, non prominent. Base. Semi-flared. Shallow. Stem cavity. Average depth of the stem cavity is about 3.0 millimeters. Average width is about 4.0 to 5.0 millimeters.

*Fruit skin*.—Thickness. Considered smooth and medium thick, and tenacious to the flesh depending on stage of maturity. Tenacity. Tenacious to flesh. Texture. Smooth. Taste. Semi-sweet, sugared, aromatic. Tendency to crack. None.

*Color*.—Blush color. This blush color is a homogenous red (RHS RED 53 A or RHS RED 46 A) on the whole fruit. Fruit stem. Medium in length, approximately 35.0 to 42.0 millimeters. The stem is firmly attached to the fruit. Diameter. Approximately 1.5 millimeters. Color. Light green (RHS YELLOW GREEN 144 B).

*Flesh*.—Ripens. Homogenous and regular. Texture. Very crunchy, luscious, juicy. Fibers. No fibers. Firmness. Very firm. Aroma. Pronounced aroma. Eating quality. Very good, very sweet, aromatic. Flavor. Semi-sweet, very sugared, aromatic. Slow acidic level. Juicy and aromatic. Juice. Large amount, very juicy. Color of juice is considered pink red (RHS PURPLE 63 A). Brix. Superior to 15.0 degrees until more or less 20.0 degrees, varies slightly with amount of fruit per tree and climatic conditions. Color. Red (RHS RED 36 D) at ripening time; with a slightly red pigmentation (RHS RED 53 B) near the apex and around the stone.

Stone:

*Type*.—Semi-Clingstone at fruits picking.

*Size*.—Medium for the variety.

*Length*.—Average 10.0 millimeters. A

*Width*.—Average width 8.5 millimeters.

*Diameter*.—Average diameter 6.5 millimeters.

*Form*.—Round to slightly elliptic.

*Base*.—Generally round.

*Apex*.—Round.

*Stone cavity*.—Small to medium with a form and dimensions corresponding to the stone's dimensions.

*Stone surface*.—Surface texture. Smooth. Ridges. None, smooth. Tendency to split. Splitting is absent.

*Ventral edge*.—Width. Very shallow, more or less 1.0 millimeter.

*Dorsal edge*.—Shape. Full, with a slight relief. Stone color. The color of the dry stone is yellow (RHS GREYED YELLOW 161 D). Tendency to split. None.

*Kernel*.—Size. Medium. Length. About 8.0 millimeters. Width. About 5.0 millimeters. Thickness. About 4.0 millimeters. Form. Elliptic, with a sharp apex and a round base. Pellicle. Not pubescent. Color. The kernel skin is orange brown (RHS GREYED YELLOW 162 D). The almond, which is the seed of the kernel, is cream-white (RHS WHITE 155 B). The kernel and its embryo are mature at the time of fruit maturity.

Use: Dessert. Fresh products.

*Market*.—Local and long distance. On the tree fruits can stay 10 days while keeping good gustative qualities. The lifetime after picking is also good.

Keeping quality: Good, held well for 30 days in cold storage at 2° C. and maintained good appearance and eating quality.

Shipping quality: Good, showed minimal bruising or scarring during picking, packing and shipping trials.

Plant/fruit disease resistance/susceptibility: Specific tests were run with regards to *Monilia* and 'FIRELAM' variety seems to be low sensitive to *Monilia*. Moreover 'FIRELAM' is low sensitive to other observed pathologies, to rupture and to conservation pathologies. "To be low sensitive" means that the variety 'FIRELAM' resists to *Monilia* and can present only minor symptoms which do not prevent its development.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of cherry tree, substantially as illustrated and described, characterized by its fruit and especially by its large size, its dark red skin color, its firmness, good flavor and eating quality; the fruit is further characterized by its good handling and storage qualities.

* * * * *